United States Patent [19]
Boynton

[11] Patent Number: 5,128,101
[45] Date of Patent: Jul. 7, 1992

[54] STERILIZATION WITH ETHYLENE OXIDE

[75] Inventor: John Boynton, Pineville, La.

[73] Assignee: The Kendall Company, Mansfield, Mass.

[21] Appl. No.: 497,457

[22] Filed: Mar. 21, 1990

[51] Int. Cl.$^5$ .............................................. A61L 2/00
[52] U.S. Cl. ....................................... 422/31; 422/34; 422/33; 422/2
[58] Field of Search ................. 422/2, 3, 31, 32, 33, 422/34, 111, 295, 298

[56] References Cited

U.S. PATENT DOCUMENTS

| | | | |
|---|---|---|---|
| 3,238,096 | 3/1966 | Kaye | 422/2 |
| 3,372,980 | 3/1968 | Satas | 422/2 |
| 3,549,312 | 12/1970 | Ernst | 422/3 |
| 3,761,224 | 9/1975 | Ernst | 422/3 |
| 3,989,461 | 11/1976 | Skocypec et al. | 422/3 |
| 4,130,393 | 12/1978 | Fox | 422/31 |
| 4,301,113 | 11/1981 | Alguire et al. | 422/2 |
| 4,637,916 | 1/1987 | Hennebert et al. | 422/295 |
| 4,812,292 | 3/1989 | Joslyn | 422/31 |
| 4,822,563 | 4/1989 | Joslyn | 422/31 |
| 4,954,315 | 9/1990 | Brahmbhatt | 422/34 |

FOREIGN PATENT DOCUMENTS 664895  6/1963  Canada .................... 422/34

Primary Examiner—Robert J. Warden
Assistant Examiner—Theresa A. Trembley
Attorney, Agent, or Firm—Alvin Isaacs

[57] ABSTRACT

A method of treating an article with a mixture of ethylene oxide gas, air, and an inert gas which makes possible reuse of the ethylene oxide for an indefinite number of successive treatment cycles. The gas mixture is refortified with ethylene oxide when necessary. Nonflammability is maintained by removing air from the treatment tank before the mixture is admitted into the tank by the evacuation of the tank to a predetermined pressure, the admitting of an inert gas to the tank to a predetermined pressure, and the subsequent removal of the resulting air and inert gas mixture from the tank by evacuation to a predetermined pressure, the air removal resulting in an air proportion less than or equal to that proportion residing in the treatment mixture that is maintained in the holding tank.

7 Claims, 2 Drawing Sheets

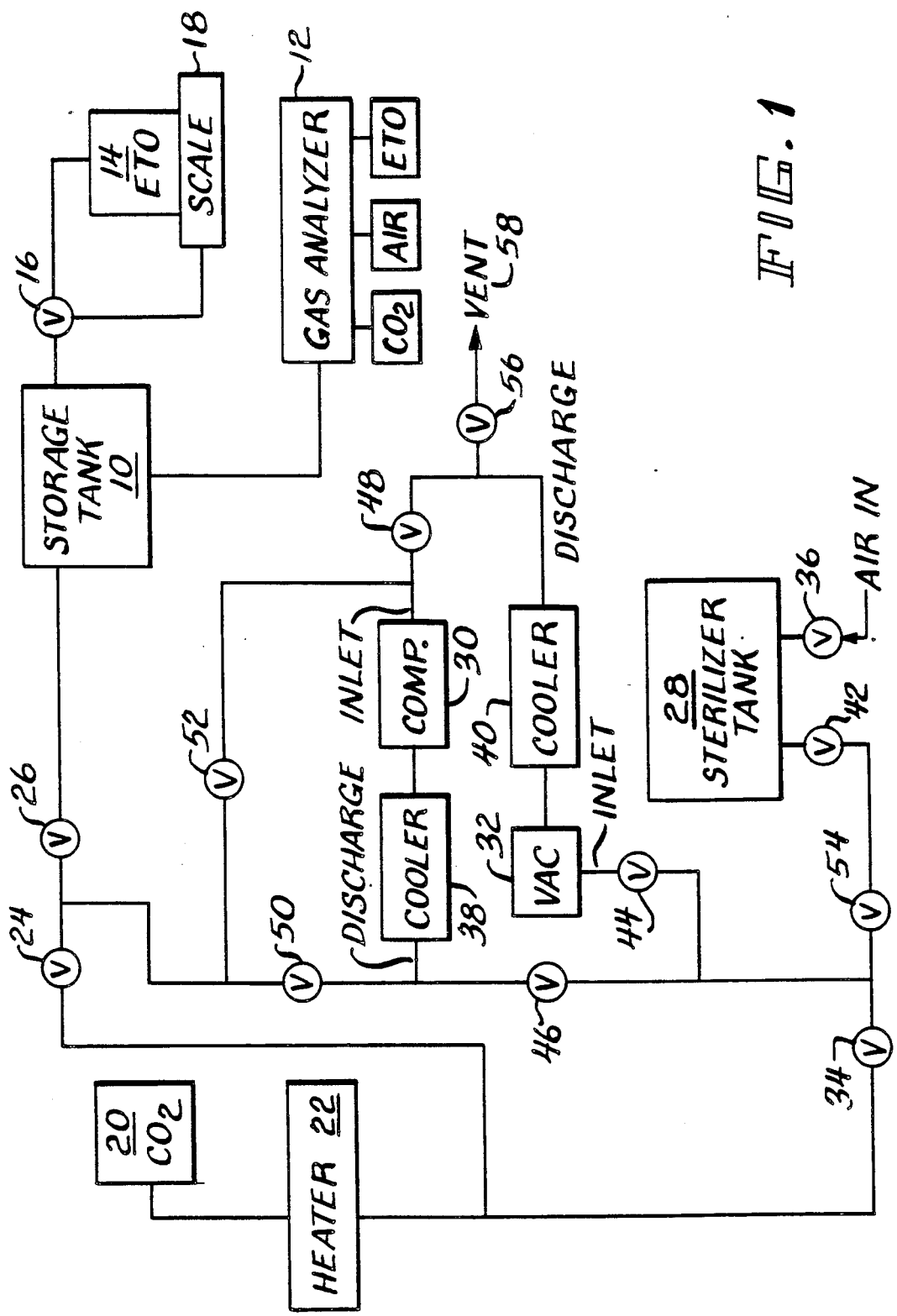

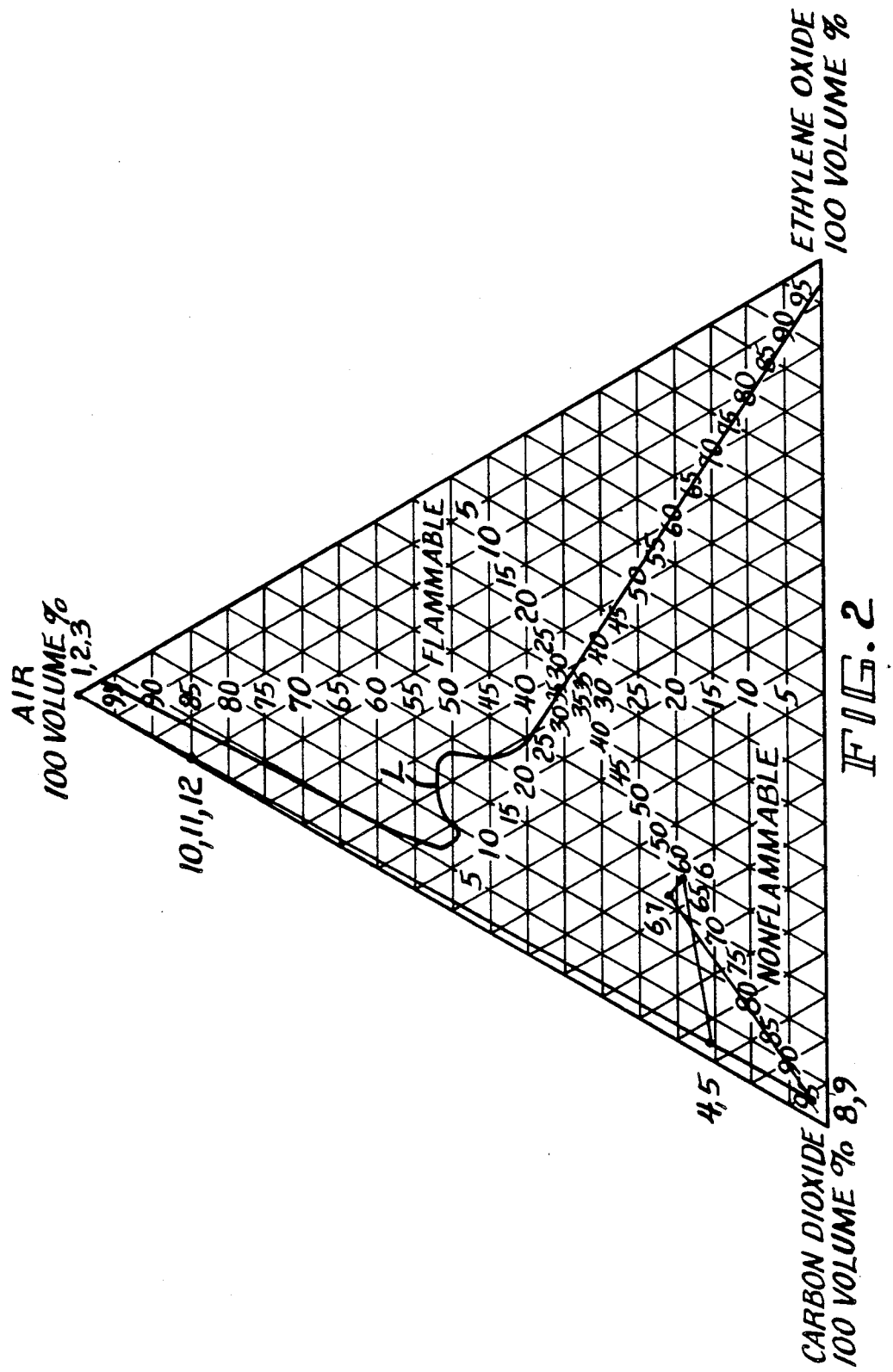

STERILIZATION WITH ETHYLENE OXIDE

BACKGROUND OF THE INVENTION

This invention relates to the treatment of articles by subjecting them to a mixture of ethylene oxide and an inert gas and, more specifically, to the use of such mixture for an indefinite number of successive treatment cycles. While various treatments with ethylene oxide are known, e.g. decontamination of spices, the most common one, and the treatment to which this invention is particularly directed, is that of sterilization. Accordingly, the invention will be described in detail hereinafter for purposes of illustration by reference to the art of sterilization with ethylene oxide.

Ethylene oxide gas is widely used as a sterilizing agent in spite of its known problems of flammability, as described in Industrial and Engineering Chemistry, June 1950, at pages 1251–1258. For this reason, it is usually mixed with an inert gas, such as carbon dioxide, nitrogen or one of the halogenated hydrocarbons, in a proportion of about 10% to perhaps 30% of ethylene oxide.

By reason of the cost of such mixtures, it is desirable to reuse them for as many cycles as possible, as is discussed in Satus U.S. Pat. No. 3,372,980; Ernst U.S. Pat. No. 3,549,312 and Skocypec et al U.S. Pat. No. 3,989,461.

However, with multiple sterilization cycles, the mixture acquires a small amount of air each time it is reused, so that the increasing proportion of air in the mixture after a number of reuse cycles produces a mixture which approaches the region of flammability. Satus solves the problem by venting the entire mixture before reaching the region of flammability and replacing it with an air-free mixture. Although this is effective from the standpoint of safety, it is expensive in its utilization of gas mixtures. Ernst and Skocypec et al both use fluorinated hydrocarbons as their inert gas for reuse, the air being separated during the condensation. These systems have the disadvantage of necessitating the use of relatively expensive inert gases which can be condensed to a liquid at relatively high temperatures. They are not economically feasible for low temperature condensing gases such as carbon dioxide and nitrogen which cannot be so readily condensed.

U.S Pat. No. 4,130,393 issued to Fox relates to an improvement in procedure for sterilization with and the recycling of ethylene oxide and has for its primary task to provide a method of reuse of a mixture of ethylene oxide and an inert gas for an indefinite number of successive sterilization cycles without condensing the mixture.

In accordance with the invention described and claimed in the aforementioned patent, this task is solved by providing a procedure for sterilizing successive loads with a nonflammable gas mixture containing at least 10 percent ethylene oxide and an inert gas wherein the gas mixture is recirculated to a storage tank after each sterilization cycle while continuously maintaining it as a gas and refortifying it by the addition of substantially pure ethylene oxide to maintain a percentage of ethylene oxide of at least 10 percent for each sterilization cycle, the mixture acquiring a small amount of air during each sterilization cycle for which it is used, the refortification procedure with ethylene oxide and the acquisition of air resulting from each successive sterilization cycle being characterized as having at least 10 percent ethylene oxide, a decreasing proportion of inert gas and an increasing proportion of air; periodically venting only a fraction of this mixture whenever the increasing proportion of air produces a mixture approaching flammability and increasing the proportion of inert gas in the mixture to reduce the proportion of air while retaining the proportion of ethylene oxide at least 10 percent; and thereafter continuing sterilizing successive loads and repeating the above procedures prior to each such successive sterilization.

The the foregoing process described in U.S. Pat. No. 4,130,393 constitutes a significant improvement in the recovery and reuse of the expensive ethylene oxide sterilizing gas while precluding the sterilizing gas mixture from achieving percentages of air in the mixture from being sufficiently great, e.g. on the order of 50 percent, so as to approach the percentage where the mixture is flammable.

Nevertheless, the requirement to periodically vent a proportion of the mixture prior to the next successive batch sterilization does present certain significant disadvantages inherent in the venting of the ethylene oxide.

With the process described in the aforementioned Fox patent, it is not possible to recover more than 75 percent of the ethylene oxide, a costly loss of the ethylene oxide.

More importantly, since at least 25 percent of the ethylene oxide is vented, existing safety and health regulations by such regulatory bodies as local OSHA and EPA administrations will not permit plant usage of the system without the use of scrubbers or other ethylene oxide abatement (capture) equipment.

The present invention is directed to improving the recovery level to a significantly higher level, e.g. on the order of that obtainable with the abatement equipment, thereby making the process acceptable for plant use without the need for such expensive equipment.

Accordingly, and stated more simply, the present invention is directed to a significantly more cost-effective procedure in the manufacture of sterile medical or other articles utilizing ethylene oxide as the sterilizing medium.

SUMMARY OF THE INVENTION

In accordance with the present invention the aforementioned task is solved in a simple and elegant manner by preventing the gas mixture from acquiring additional air during each successive treatment cycle.

This is accomplished by the steps of:

(1) drawing a vacuum on the chamber containing the article or articles to be treated;

(2) introducing an inert gas into the thus evacuated chamber;

(3) evacuating the chamber a second time, whereby the air concentration in the chamber at the time the recycled gas mixture is introduced is no greater than that of the gas mixture and preferably substantially less than that in the mixture; and (4) thereafter recycling the gas mixture into the treatment chamber.

BRIEF DESCRIPTION OF THE DRAWINGS

FIG. 1 is a schematic drawing of a sterilizing system useful in the practice of the present invention, and FIG. 2 is a ternary diagram of mixtures of ethylene oxide, carbon dioxide and air, showing its flammable and nonflammable regions and certain other aspects of the present invention.

DETAILED DESCRIPTION OF THE INVENTION

As was heretofore mentioned, the present invention is particularly directed to the sterilization procedure in the manufacture of sterile products such as would be used for health care, which procedures utilize an ethylene oxide/inert gas sterilizing mixture. In such procedures, it is well known in the art to recycle the gas mixture for successive sterilizing batches.

As was also heretofore stated, the primary task of the invention is to increase the recovery rate of the recycled ethylene oxide significantly to a level where abatement equipment is not required to satisfy safety and health regulations limiting the amount of ethylene oxide which can be vented to the air. An additional advantage in solving this task is the increased savings in production costs resulting from the increased recovery of the expensive ethylene oxide.

In its broadest terms, the task of this invention can be stated to be to provide a more efficient and cost-effective system for in-plant sterilization utilizing ethylene oxide as the sterilant.

In one aspect of the invention, there is provided, a method of sterilizing successive loads with a recycled gas mixture containing ethylene oxide gas which is refortified with substantially pure ethylene oxide as required to maintain a proportion of at least 10% ethylene oxide in the mixture which consists of ethylene oxide, an inert gas, and air. The mixture is maintained in a nonflammable condition by controlling the quantity of air that enters the recycled gas mixture by evacuating the sterilizing tank, increasing the pressure in the sterilizing tank with an inert gas such that the gas mixture in the sterilizing tank contains a proportion of air between 10% and 25%, and evacuating the sterilizing tank again before the sterilant mixture is admitted to the sterilizing tank, sterilizing loads in succession in a sterilizing tank, reusing the mixture by circulating it to a storage tank while continuously maintaining it as a gas and refortifying it by the addition of substantially pure ethylene oxide so that the proportion of ethylene oxide initially present in the mixture sterilizing each load is at least 10% and the air present in the mixture sterilizing each is between about 10% and 25%, whereby an indefinite number of successive loads may be sterilized without entering the region of flammability of the mixture without venting a portion of said gas mixture and subsequently replacing the vented portion with substantially pure ethylene oxide and an inert gas or condensing and separating the gas into components, retaining the useful components and disposing of the balance, to maintain the nonflammability of the mixture.

In another aspect, the present invention provides a method of mixing ethylene oxide and an inert gas, preferably carbon dioxide, and air to provide a uniform gaseous mixture of predetermined proportions having at least 10% ethylene oxide and 10%–25% air, comprising: first evacuating an enclosed container containing air to a predetermined pressure, providing a source of inert gas, removing the inert gas from its source, heating it, preferably to a temperature of at least 200 degrees Fahrenheit, and introducing it into the evacuated enclosed container to increase the pressure in the enclose container to a predetermined level, and introducing a predetermined quantity of ethylene oxide from a liquid source thereof into the enclosed container, the introduction of ethylene oxide being carried out in a nonflammable condition due to the method described.

The above and still further objects and features of the present invention will in part be obvious and will in part be apparent from the following detailed description taken together with the accompanying drawings.

In the system of FIG. 1 is shown an enclosed storage tank 10 provided with a gas analyzer 12 providing indications of the proportions of ethylene oxide, carbon dioxide, and air in storage tank 10. A source of liquid ethylene oxide 14 is connected to storage tank 10 through ethylene oxide valve 16. Valve 16 may be operated by a preset scale 18 so that a predetermined quantity of ethylene oxide may be automatically introduced into storage tank 10. A source of liquid carbon dioxide 20 is also connected to storage tank 10 through heater 22, valve 24, and valve 26.

Sterilizer tank 28 is connected to storage tank 10 both through compressor 30 for pumping the sterilant mixture into sterilizer tank 28 and through vacuum pump 32 for removing the gas mixture from the sterilizer tank 28 into storage tank 10, the vacuum pump 32 consisting of a system of pumps wherein a constant flow rate is maintained by the staging of pumping mechanisms if and when the capacity of a single pump is reached. The sterilizer tank 28 is connected to the carbon dioxide supply 20 and heater 22 through valve 34. The sterilizer tank 28 is connected to the atmosphere by valve 36.

The compressor 30 is also provided with a conventional gas cooler 38. The vacuum pump 32 is also provided with a cooler 40. Valves 42, 44, 46, 48, 50, 52 and 26 provide directional control of the gases through the vacuum pump 32 and compressor 30. Valve 54 is a proportioning valve that maintains a constant rate of flow into and out of the sterilizer tank 28. Valve 56 connects the pumping and valve system comprised of vacuum pump 32, cooler 40, compressor 38, cooler 30, valves 42, 54, 46, 48, 50, 52 and 26 to the atmosphere for the purpose of evacuations of the sterilizing tank 28 and storage tank 10.

In order to initially fill storage tank 10 with a mixture of ethylene oxide, air, and carbon dioxide, storage tank 10 is suitably evacuated by opening valves 26, 50, 46, 44 and 56 with all the other valves being closed. Vacuum pump 32 can then be operated to evacuate storage tank 10 through vent 58 to a predetermined pressure, preferably 2-3 psia. Valves 26, 50, 46, 44 and 56 are then closed.

Valves 24 and 26 are then opened to introduce carbon dioxide into the storage tank 10 through heater 22. Heater 22 is operated to heat the carbon dioxide to a temperature of about 200–250 degrees F. preferably 225 degrees F., to prevent the condensation of ethylene oxide in storage tank 10 by reason of the cooling effect of introducing ethylene oxide into a cold atmosphere. The introduction of carbon dioxide proceeds until the desired proportions of carbon dioxide and air are present, preferably 95% carbon dioxide and 5% air, as can be predetermined by empirical methods, calculations or by the indication of gas analyzer 12. Valves 24 and 26 are then closed.

Scale 18 is then set to the desired quantity of ethylene oxide to open valve 16 to introduce a predetermined quantity of ethylene oxide from source 14 into storage tank 10, after which valve 16 automatically closes. For effective sterilization it is important that at least 10% ethylene oxide be present in storage tank 10. However, higher proportions of ethylene oxide, up to 35%, can be employed.

The successive sterilizing cycles are then begun by sterilizing loads in succession in sterilizing tank 28, reusing the mixture by recirculating it to storage tank 10, while continuously maintaining it as a gas, and refortifying it by the addition of substantially pure ethylene oxide so that the proportion of ethylene oxide initially present in the mixture sterilizing each load is at least 10%.

To prevent the contamination of the sterilant mixture by means of an increasing proportion of air due to that quantity of air that resides in sterilizing tank 28 in the evacuated condition, carbon dioxide is admitted to sterilizing tank 28 by opening valves 42, 54 and 34, allowing carbon dioxide to flow from source 20 through heater 22 and into sterilizer tank 28. When a predetermined pressure is reached that provides a proportion of air in sterilizer tank 28 that is less than or equal to that proportion of air in storage tank 10, valves 42, 54 and 34 are closed. Valves 42, 54, 44 and 56 are opened and vacuum pump 32 and cooler 40 operated to evacuate sterilizer tank 28, thereby removing a portion of the carbon dioxide and air mixture from sterilizer tank 28. Sterilizing of successive loads proceeds without an increase in the proportion of air present in the sterilant mixture, as shown on FIG. 2.

Although it is important to maintain the proportion of air in the mixture sufficiently low to prevent the mixture from approaching the flammable region of the mixture when present in the system including storage tank 10 and sterilizer tank 28, the mixture can be safely vented to the atmosphere without danger of fire or explosion if done under controlled conditions.

Referring again to FIG. 1, in a sterilization system for use with the present invention in which the sterilizer and storage tanks both have a volume of about 750–1400 cubic feet, although sterilizer tank 28 and the storage tank 10 can be of identical volume to simplify the empirical methods or calculations required to operate the sterilization system, and the storage tank has been filled as described above, the following procedure is typical:

1. The sterilizer tank 28 is heated to approximately 120–140 degrees F. and maintained at that temperature.

2. A load to substantially fill sterilizer tank 28 is placed inside sterilizer tank 28 and the door on sterilizer tank 28 is closed.

3. The sterilizer tank 28 is evacuated to a pressure of about 1–3 psia by opening valves 42, 54, 44 and 56 and operating the vacuum pump 32, discharging through cooler 40 to vent 58 with all other valves closed, valves 42, 54, 44 and 56 closing and the operation of the vacuum pump being stopped when the evacuation is complete.

4. Valves 42, 54 and 34 are opened to admit carbon dioxide from source 20 through heater 22 to sterilizer tank 28 until a predetermined pressure is reached, at which time valves 42, 54 and 34 are closed.

5. The sterilizer tank 28 is evacuated to a pressure of about 1–3 psia by opening valves 42, 54, 44 and 56 and operating the vacuum pump 32 discharging through cooler 40 to vent 58 with all other valves closed, valves 42, 54, 44 and 56 closing and the operation of the vacuum pump being stopped when the evacuation is complete.

6. Valves 26, 52, 46, 54 and 42 are opened and compressor 30 operated through cooler 38 to remove sterilant mixture from storage tank 10 and to admit the sterilant mixture to sterilizer tank 28 until a predetermined pressure is achieved in the sterilizer tank 28, at which time valves 26, 52, 46, 54 and 42 are closed and compressor 30 operation is stopped. The load is left to sterilize.

7. Valves 42, 54, 44, 48, 52 and 26 are opened and vacuum pump 32 operated through cooler 40 to remove sterilant mixture from storage tank 10 until such time as the capacity of vacuum pump 32 has been reached by virtue of the differential pressure across the vacuum pump 32, at which time valve 52 is closed and valve 50 is opened and compressor 30 is operated to act in assistance to vacuum pump 32 in removing sterilant mixture from sterilizer tank 28 and admitting the sterilant mixture to storage tank 10 until the pressure in sterilizer tank 28 has been reduced to about 1–3 psia, at which time valves 26, 50, 48, 44, 54 and 42 are closed and the vacuum pump 32 and compressor 30 operation is stopped.

8. Valves 34, 54 and 42 are opened to admit carbon dioxide from carbon dioxide source 20 through heater 22 into sterilizer tank 28 until a predetermined pressure is reached, at which time valves 34, 54 and 42 are closed.

9. The sterilizer tank 28 is evacuated to a pressure of about 1–3 psia by opening valves 42, 54, 44 and 56 and operating the vacuum pump 32 discharging through cooler 40 to vent 58 with all other valves closed, valves 42, 54, 44 56 closing and the operation of the vacuum pump being stopped when the evacuation is complete.

11. Valve 36 is closed when atmosphere pressure is attained in sterilizer tank 28.

12. By virtue of the fact that a portion of the recycled sterilant mixture is lost during a sterilization cycle by means of quantities of the sterilant mixture remaining in pumps, valves, and piping which are subsequently passed to vent 58 in the steps required to evacuate sterilizer tank 28, and that quantity required for analysis by gas analyzer 12, the proportion of carbon dioxide in the sterilant mixture maintained in storage tank 10 is increased by opening valves 26 and 24 and admitting carbon dioxide from source 20 through heater 22 into storage tank 10 until a predetermined pressure is achieved, the predetermination being based on empirical methods, calculations or by the indication of gas analyzer 12.

13. Sterilizer tank 28 is unloaded.

14. Repeat steps (2) through (12) an indefinite number of times without the venting of the entire gas mixture or a portion of the mixture from the system while maintaining the mixture in the nonflammable condition shown of FIG. 2.

With reference to the ternary diagram of FIG. 2, it will be seen that at all volume percentages to the left of line L a nonflammable mixture is obtained; while at all volume percentages on the right side of line L a flamable mixture is present.

In the diagram of FIG. 2, the numerals, 1–12 refer to the above-mentioned steps 1–12 of the novel process of this invention. Thus, the points designated as 1, 2, 3; 4, 5; 6, 7; 8, 9; and 10, 11, 12 respectively, indicate the volume percentages of the ethylene oxide mixture at the indicated twelve steps, e.g. the point designated 1, 2, 3 signifies the volume percentages at steps 1, 2, 3; the point 4, 5 signifies the volume percentages at steps 4, 5, etc. If one then draws a line from point 1, 2, 3 to point 4, 5, from point 4, 5 to point 6, 7, then to point 8, 9 and finally up to point 10, 11, 12 as shown in FIG. 2, it will be seen that at all times a nonflammable mixture is maintained.

By way of recapitulation, the present invention provides a highly efficient system for successive batch sterilizations with recycled ethylene oxide sterilant. The system described in detail in the foregoing description will improve the ethylene oxide recovery process from the 75 percent obtainable with the system described in U.S. Pat. No. 4,130,393 to on the order of 97 percent, an improvement of about 30 percent.

This improved recovery makes it possible for one employing the process of this invention to meet or exceed ethylene oxide safety emission level regulations without the use of costly discrete abatement equipment in the process.

It will be appreciated that various modifications and changes may be made in the light of the foregoing description without departing from the scope of the invention herein contemplated.

For example, while reference has been made to the use of carbon dioxide in admixture with the ethylene oxide sterilant, the use of other inert gases such as nitrogen are also contemplated.

Since certain changes may be made without departing from the scope of the invention herein described, it is intended that all matter contained in the foregoing description along with the accompanying drawing shall be taken as illustrative and not in a limiting sense.

What is claimed is:

1. In a method of treating an indefinite number of successive loads of articles to be treated with a noflammable gas mixture containing at least 10 percent ethylene oxide gas by volume, an inert gas and air, comprising the steps of treating the successive loads in individual treatment cycles in succession in a treatment chamber in which the treating gas mixture containing the ethylene oxide is recirculated after each treatment cycle to a storage tank where it is refortified by the addition of substantially pure ethylene oxide so that the proportion of ethylene oxide for each subsequent treating cycle is at least ten percent, introducing the next load to be treated into the treatment chamber, drawing a vacuum in the treatment chamber and thereafter circulating the refortified gas mixture back to the evacuated treating chamber for treating the next load contained therein, the method further comprising the step of preventing an increase in the proportion of air in the mixture from approaching the proportion of flammability of the gas mixture;

the improvement wherein preventing the increase of air so as to maintain the mixture nonflammable comprises the steps of:

(1) introducing an inert gas into the evacuated treatment chamber containing the load to be treated prior to introducing the treating gas mixture so that the gas in the chamber consists of a mixture of air present after drawing the vacuum to evacuate the chamber and the inert gas so introduced, the percentage of air in the chamber in the air and inert gas mixture being no greater than the percentage of air in the refortified treating gas mixture in the storage tank;

(2) and thereafter drawing a second vacuum on the treatment chamber containing the load to be treated and the mixture of inert gas and air prior to circulating the refortified gas mixture back to the treating chamber, whereby the percentage of air in the gas mixture is not increased by the addition of any amounts of air in the treating chamber in each successive cycle, thereby obviating the need to vent any of the mixture to the atmosphere to maintain the treating gas mixture nonflammable.

2. A method as defined in claim 1 wherein the percentage of air by volume in said gas mixture is maintained between about 10 to about 25 percent for each successive treatment cycle.

3. A method as defined in claim 1 wherein said vacuum drawn on said chamber is to a pressure of from about 1 to about 3 psia.

4. A process as defined in claim 1 wherein said inert gas comprises carbon dioxide.

5. In a method of sterilizing an indefinite number of loads in successive sterilization cycles in a sterilizing chamber with a nonflammable gas mixture containing at least ten percent ethylene oxide gas, by volume, an inert gas and air, the method including the step of recirculating the gas mixture to the sterilizing chamber after each sterilization cycle while continuously maintaining it as a gas having at least ten percent ethylene oxide gas by volume;

the improvement comprising the step of:

(1) providing a mixture of inert gas and air within the sterilizing chamber before recirculating the sterilant gas mixture thereto, whereby to render the concentration of air in the chamber prior to recirculation of the gas sterilizing mixture to no greater than the concentration of air in the recirculating sterilant mixture, thereby obviating the need for periodic venting of a fraction of the sterilant mixture when the proportion of air from each successive cycle increases progressively to provide a mixture approaching flammability.

6. A method as defined in claim 5 wherein the percentage by volume of air in said sterilant mixture is maintained at from about 10 to about 25 percent.

7. A method as defined in claim 5 wherein said inert gas is carbon dioxide.

* * * * *